ns Measurements", 1982, Mashinostroenie Publ. House, pp. 17-19.

*Primary Examiner*—Tom Noland
*Attorney, Agent, or Firm*—Fleit, Jacobson, Cohen, Price, Holman & Stern

United States Patent
Bakirov et al.

Patent Number: 5,062,293
Date of Patent: Nov. 5, 1991

[54] APPARATUS FOR MEASURING HARDNESS OF MATERIALS

[75] Inventors: Murat B. Bakirov, Zhukovsky; Alexandr F. Getman, Moscow; Boris I. Gribov, Sofrino; Andrei A. Bordjugovsky; Alexandra P. Klimenok, both of Moscow, all of U.S.S.R.

[73] Assignee: Nauchno-Proizvodstvennoe Objedinenie, Moscow, U.S.S.R.

[21] Appl. No.: 461,749

[22] Filed: Jan. 8, 1990

[51] Int. Cl.$^5$ .............................................. G01N 3/42
[52] U.S. Cl. ........................................... 73/81; 73/83
[58] Field of Search ................................ 73/78, 81-85

[56] References Cited

U.S. PATENT DOCUMENTS

| 2,473,179 | 6/1949 | Sklar | 73/83 |
|---|---|---|---|
| 3,123,997 | 3/1964 | Cosner | 73/81 |
| 3,590,630 | 7/1971 | Ericksson | 73/83 |
| 3,949,600 | 4/1976 | Iwasaki | 73/83 |
| 4,104,901 | 8/1978 | Sidaway | 73/81 |
| 4,196,616 | 4/1980 | Argabrite et al. | 73/81 |
| 4,312,220 | 1/1982 | Borgersen et al. | 73/81 |

FOREIGN PATENT DOCUMENTS 170721 6/1965 U.S.S.R. .

OTHER PUBLICATIONS

Yu. A. Mayorov, F. M. Nikitin, "Instruments for Hard-

[57] ABSTRACT

An apparatus for measuring hardness of materials has an indentor to be pressed into the surface of material, a rod in the form of a center plate having a shank rigidly secured to one end thereof and the indentor rigidly secured to the other end thereof. The apparatus also has a dynamometric gauge having a first branch thereof with a hole in which the shank of the rod is received. A second branch of the dynamometric gauge supports a spindle of a device for loading the indentor. One of the branches of the dynamometric gauge carries at least one pick-up for measuring the load at the indentor engageable with the other branch of the dynamometric gauge. The apparatus also has a device for measuring the depth of penetration of the indentor into the surface of material in the form of a frame having its opposed bars enclosing the first branch of the dynamometric gauge. A tip is rigidly secured to the first bar of the frame located between the surface of material and the first branch of the dynamometric gauge, the indentor being received in the tip. The first branch of the dynamometric gauge carries a pick-up for measuring the depth of penetration of the indentor into the surface of material engageable with the frame.

39 Claims, 7 Drawing Sheets

APPARATUS FOR MEASURING HARDNESS OF MATERIALS

This invention relates to the field of investigation into physical properties of materials, and more specifically, it deals with apparatuses for measuring hardnesses of materials.

The invention will find application in determining mechanical properties of metal in the casing of a nuclear power reactor during the whole service life.

BACKGROUND OF THE INVENTION

Known methods of determining mechanical properties of solids are based on experimental relationships of mechanical properties versus hardness of materials. A hard alloy member in the form of a sphere or cone is caused to penetrate the surface of an object being studied to produce an impression. Hardness of materials is determined as the ratio of a force pressing the indentor to the area of the impression or depth of penetration of the indentor into the surface of material. Using experimental formulae for calculations, standard mechanical properties such as ultimate strength and yield limit are determined from the hardness value. If the configuration of the impression is determined using optical test equipment after the load has been relieved from the surface of material, accuracy of hardness measurement is low since after the load removal from the surface of the material the configuration of the impression changes so as to lower accuracy of hardness measurement.

With an automatic measurement of the depth of penetration of the indentor into the surface of material during penetration of the indentor under a preset load it is not possible to record a complicated mode of material deformation, i.e. the relationship of the load at the indentor versus the depth of penetration of the indentor into the surface of material and penetration time. This method does not allow delicate processes of deformation in the indent to be studied thus substantially reducing informativity of the method.

Widely known in the art is an automatic durometer (see, e.g. U.S.S.R. publication 170721), comprising a dynamometric gauge having a first branch having a composite rod consisting of a pair of vertical movable parts mounted for movement along guides of an inner movable cylinder. The inner movable cylinder is mounted for movement along guides of a fixed outer cylinder, the inner cylinder being biased by a spring with respect to the outer cylinder. A stop washer is biased by a spring to the end of the inner movable cylinder and encloses an indentor which is secured to the lower vertical part of the composite rod. Displacement of the indentor with respect to the stop washer is measured by means of a dial gauge mounted on the fixed outer cylinder and engageable with the lower vertical part of the composite rod. The apparatus also comprises a casing accommodating an indentor loading means having a spindle secured to the second branch of the dynamometric gauge and a drive for moving the spindle.

The main load of the indentor is recorded by means of an electric contact pick-up mounted on the second branch of the dynamometric gauge and cooperating with the first branch of the dynamometric gauge.

The preload is recorded by means of an electric contact pick-up provided between the first branch of the dynamometric gauge and the spindle of the drive for moving the spindle cooperating with the second branch of the dynamometric gauge.

The prior art apparatus functions automatically and allows hardness of materials to be measured with a high enough accuracy, but it cannot ensure continuous recording of load and depth of penetration of the indentor into the surface of material so as to result in a low accuracy of measurement of hardness of materials. The use of the apparatus for objects located in radioactive zones is difficult because deactivation and maintenance of the apparatus are complicated owing to the complicated structure and presence of cavities. Rapid assembly and disassembly as well as setup of the apparatus under radiation conditions are associated with high radiation exposure of operating personnel. The provision of the two coaxially mounted cylinders and composite rod of the indentor cooperating along parallel lines of guides with appropriate free fits lowers accuracy of measurement of hardness of materials especially in various positions of the apparatus in space where it is necessary to measure hardness of vertical or inclined surfaces of various parts. The apparatus does not allow delicate processes of deformation of materials to be studied.

Widely known in the art is a portable device for measuring Brinell hardness of materials (Yu. A. Mayorov, F. M. Nikitin, Instruments for Hardness Measurements (in Russian), 1982, Mashinostroenie Publishing House, Moscow. pp. 17–19; 54–55), comprising an indentor to be pressed into the surface of material and a rod in the form of a center plate having a shank at one end thereof and the indentor rigidly secured to the other end thereof. A dynamometric gauge is mounted perpendicularly with respect to the surface of material, one branch of the gauge having a hole in which the rod shank is received. The device also comprises a means for loading the indentor having a spindle mechanically coupled to a drive for its movement and mounted coaxially with the rod on the other branch of the dynamometric gauge. The means for loading the indentor is mounted in a casing. The rod shank is engageable with a means for measuring the load of the indentor or a dial gauge mounted on the casing.

The device also comprises a means for attaching the device to an object for measurements and an optical means for measuring the diameter of impression in the material, e.g. a microscope. This device allows the final result of deformation of the surface of material such as impression or indent to be recorded so that it features a low informativity as regards processes of elastic and plastic deformation of material in the indent and a low accuracy. The device cannot be used for objects located in zones with high radiation as it cannot function automatically and calls for a permanent attendance of personnel so as to result in an increase in radiation exposure of the personnel.

SUMMARY OF THE INVENTION

It is an important object of the invention to enhance accuracy in measuring hardness of materials.

Another object of the invention is to enlarge functional capabilities of the apparatus and facilitate operation and maintenance of the apparatus.

These objects are accomplished by that an apparatus for measuring hardness of materials, comprising an indentor to be pressed into the surface of material, a rod in the form of a center plate having a shank secured to one end thereof and the indentor rigidly secured to the other end thereof, a dynamometric gauge having a longitudinal plane of symmetry thereof extending perpendicularly with respect to the surface of material, a first branch having a hole in which the rod shank is received, a means for loading the indentor having a spindle mechanically coupled to a drive for its movement and mounted on the second branch of the dynamometric gauge coaxially with the rod, a casing supporting the means for loading the indentor, and at least one pick-up for measuring the load at the indentor mechanically coupled to one of the branches of the dynamometric gauge and having its sensor member engageable with the other branch of the dynamometric gauge, according to the invention, comprises a means for measuring the depth of penetration of the indentor into the surface of material which is in the form of a frame having its opposed bars enclosing the first branch of the dynamometric gauge and mounted for movement along the axis of the rod on the center plate and rod shank, respectively, an annular tip having one end thereof rigidly secured to the first bar of the frame located between the surface of material and the first branch of the dynamometric gauge, the indentor being received in the tip in a spaced relation thereto and the other end of the tip being engageable with the surface of material, the apparatus also comprising at least one pick-up for measuring the depth of penetration of the indentor into the surface of material which is mechanically coupled to the first branch of the dynamometric gauge and which has its sensor member engageable with the frame of the means for measuring the depth of penetration of the indentor into the surface of material.

To facilitate manufacture, installation and maintenance of the apparatus, it is preferred that the frame of the means for measuring the depth of penetration of the indentor into the surface of material be positioned with respect to the dynamometric gauge in such a manner that their longitudinal planes of symmetry be perpendicular with respect to each other.

To facilitate maintenance of the apparatus, it is preferred that central holes be provided in the opposed bars of the frame for measuring the depth of penetration of the indentor into the surface of material to accommodate bearings and to receive the center plate and the rod shank, respectively.

To enhance accuracy of measurement of hardness of materials, it is preferred that use be made of at least two pick-ups for measuring the indentor load and two pick-ups for measuring the depth of penetration of the indentor into the surface of material, the pick-ups for measuring the indentor load and the pick-ups for measuring the depth of penetration of the indentor into the surface of material being positioned on either side of the longitudinal plane of symmetry of the dynamometric gauge.

To enhance accuracy of measurement of hardness of materials, facilitate manufacture, installation and maintenance, it is preferred that the apparatus comprise a first auxiliary outside member supported on one of the branches of the dynamometric gauge and having at least one main hole in which at least one indentor load pick-up is rigidly secured, a second outside member supported on the other branch of the dynamometric gauge and having at least one contact land engageable with the sensor member of at least one indentor load pick-up, a third outside member supported on the first branch of the dynamometric gauge and having at least one main hole thereof in which at least one pick-up for measuring the depth of penetration of the indentor into the surface of material is rigidly secured, and a fourth outside member supported on the first bar of the frame of the means for measuring the depth of penetration of the indentor into the surface of material having at least one contact land engageable with the sensor member of at least one pick-up for measuring the depth of penetration of the indentor into the surface of material.

For enhancing accuracy of measurement of hardness of materials, it is preferred that at least one of the outside members have an auxiliary hole for receiving one end of at least one guide pin having the other end thereof journalled in a bearing which is received in at least one peripheral hole of one of the bars of the frame of the means for measuring the depth of penetration of the indentor into the surface of material.

To enhance accuracy of measurement of hardness of materials in using at least two guide pins, it is preferred that the pins be positioned on either side of the longitudinal axis of symmetry of the dynamometric gauge.

To enhance accuracy of measurement of hardness of materials, it is preferred that the apparatus comprise an elastic member having its opposed sides secured to the spindle of the means for loading the indentor on the side of the inner surface of the second branch of the dynamometric branch and to the second bar of the frame of the means for measuring the depth of penetration of the indentor into the surface of material, located between the first and second branches of the dynamometric gauge.

To enhance accuracy of measurement of hardness of materials, it is preferred that the elastic member comprise an annular spring.

To ensure remote control of the apparatus, it is preferred that the pick-ups for measuring the indentor load, the pick-ups for measuring the depth of penetration of the indentor into the surface of material, and the drive for moving the spindle of the means for loading the indentor be electrical.

To enhance accuracy of measurement of hardness of materials, it is preferred that the means for loading the indentor also comprise a worm gearing connected to the electric drive for moving the spindle and a ball-and-screw gearing operatively connected to the worm gearing and provided on the periphery of the spindle.

Owing to the employment of the means for measuring the depth of penetration of the indentor into the surface of material, comprising the frame connected to the center plate and to the rod shank, the invention allows plays in the free fit to be eliminated and lowers spurious elastic deformation of the rod so as to enhance accuracy of measurement of hardness of materials and facilitate installation, manufacture and setup of the apparatus. The apparatus has a minimized number of components the major part of which are mounted coaxially with, and symmetrically with respect to the rod thus also facilitating installation, manufacture and setup of the apparatus.

DESCRIPTION OF THE DRAWINGS

The invention will now be described with reference to specific embodiments of the apparatus for measuring hardness of materials according to the invention illustrated in the accompanying drawings, in which.

PREFERRED EMBODIMENT

Figure 1:
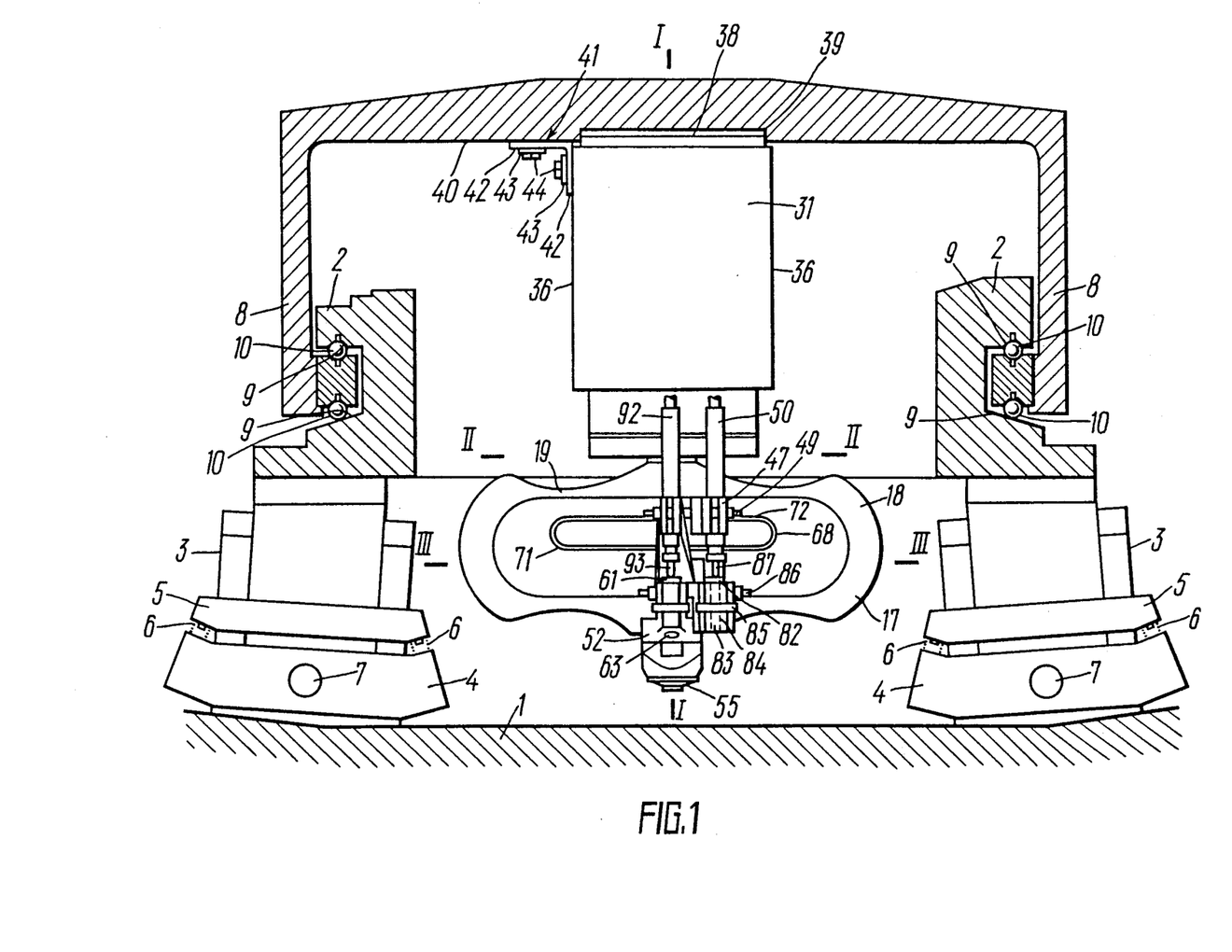
FIG. 1 is a general view (front elevation, partially in longitudinal section) of an apparatus for measuring hardness of materials showing members for attaching the apparatus to the surface of material according to the invention.

An apparatus for measuring hardness of materials is attached to a surface 1 of material (FIG. 1) by means of a support structure consisting of a bed 2 which is secured to the surface 1 of material by means of two or more pairs of electromagnets 3. Shoes 4 are secured to the ends of the electromagnets 3 and are biased by springs 6 with respect to a base 5 for rotation about an axis 7. A movable carriage 8 is mounted on the bed 2 for movement along guide planes 9 of the bed 2 by means of balls 10. The apparatus for measuring hardness of materials comprises an indentor 11 (FIG. 2) to be pressed into the surface 1 of material in the form of a ball. The apparatus also has a rod 12 in the form of a center plate 13 having an indentor 11 secured to one end thereof and a shank 14 secured to the other end thereof. The shank 14 of the rod 12 is retained by means of a key 15 in a hole 16 of a first branch 17 of a diynamometric gauge 18 which is positioned in an immediate vicinity to the surface 1 of material. The dynamometric gauge 18 is positioned in such a manner that the longitudinal axis of symmetry of the dynamometric gauge 18 extends perpendicularly with respect to the surface 1 of material.

Figure 2:
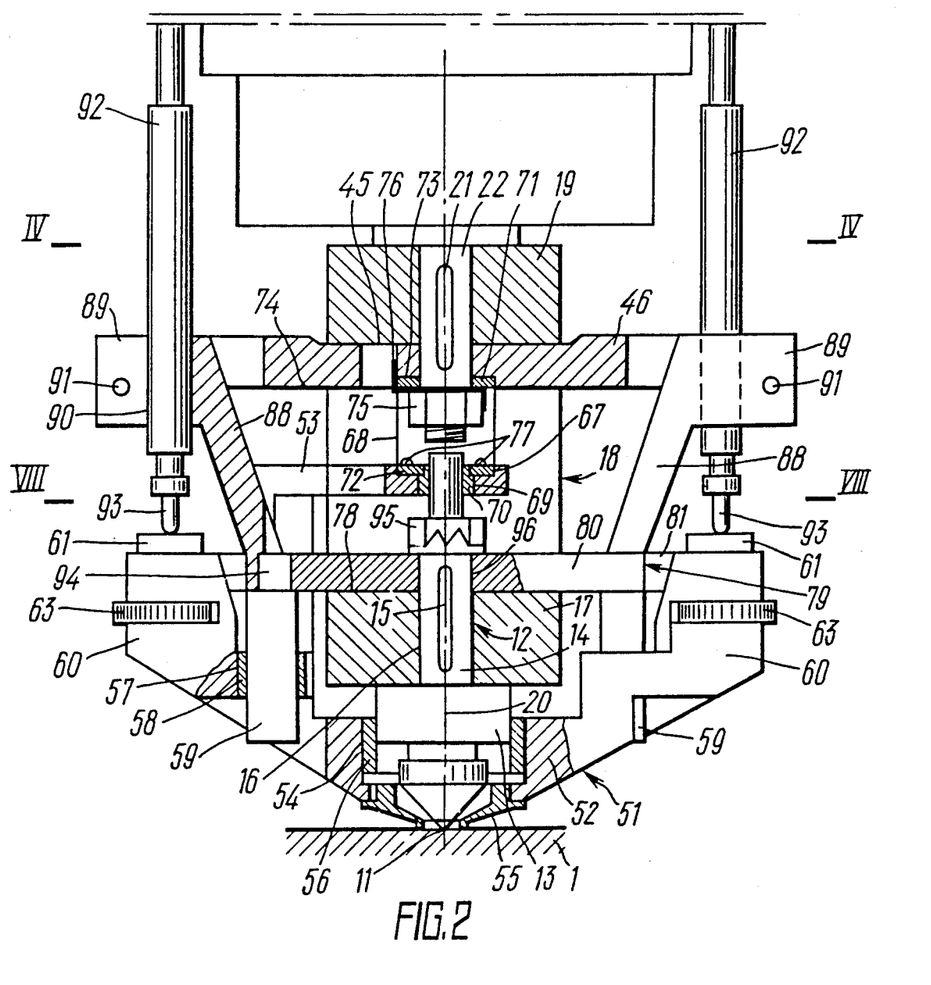
FIG. 2 is a general view (side elevation in longitudinal section) of an apparatus according to the invention.

Mounted on a second branch 19 of the dynamometric gauge 18 to extend along an axis 20 of the rod 12 is one end of a spindle 22 of a means for loading the indentor retained by means of a key 21. The means for loading the indentor comprises a drive for moving the spindle in the form of an electric motor 23 (FIG. 3) mechanically coupled to the spindle 22 by means of a worm gearing 24. The worm gearing 24 comprises a worm 25 mechanically coupled to a shaft 26 of the electric motor 23. The worm 25 meshes with a gear 27 having a bushing 28 received in its bore. The gear 27 and the bushing 28 are made to form a non-detachable joint. The bushing 28 is journalled by means of bearings 29 on an inner surface 30 of a casing 31. A pin 32 is provided on the periphery of the spindle 22 to move in a longitudinal groove 33 made in the inner surface 30 of the casing 31.

Figure 3:
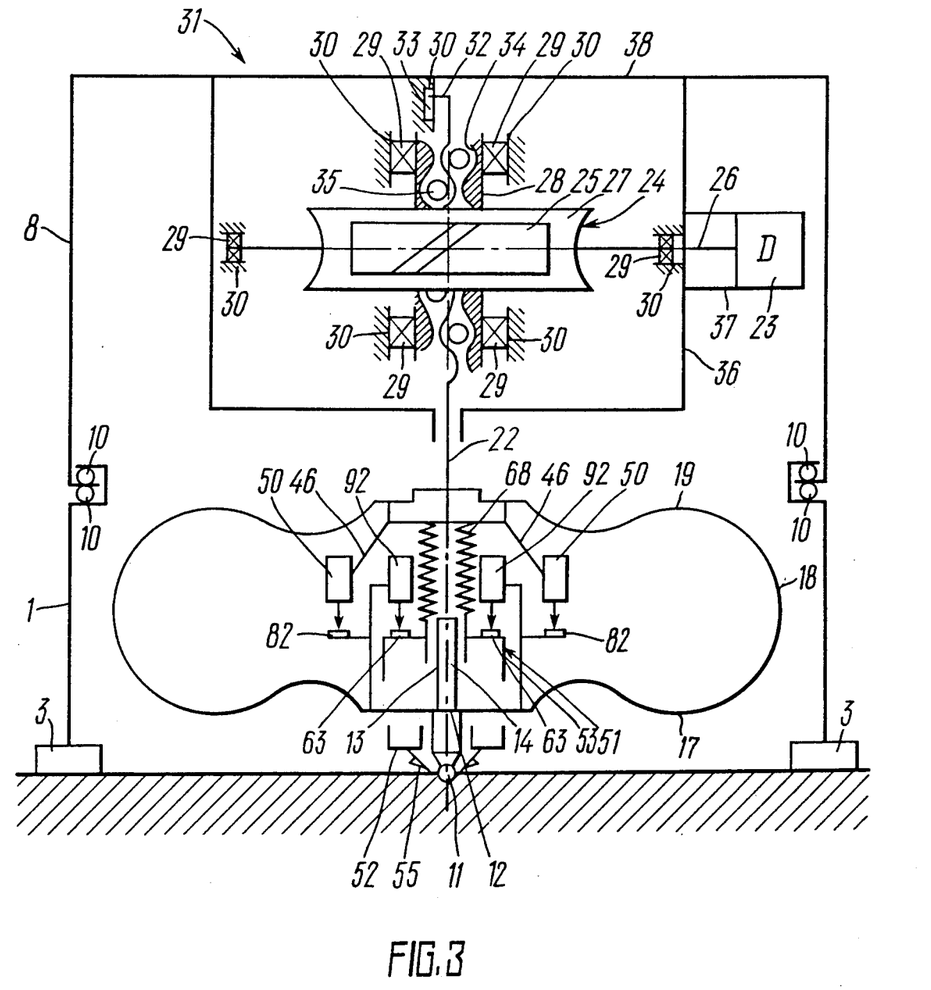
FIG. 3 is a kinematic diagram of an apparatus according to the invention.

The spindle 22 is received in a bore 34 of the bushing 28. Provided between a helical inner surface of the bore 34 of the bushing 28 and a helical periphery of the spindle 22 there is a ball-and-screw gearing in the form of a set of balls 35. The frame of the electric motor 23 is attached to an outer periphery 36 of the casing 31 by means of fasteners 37. The shaft 26 of the electric motor 23 is journalled by means of bearings 29 on the inner surface 30 of the casing 31. The upper outer surface 38 of the casing 31 is removably received in a groove 39 (FIG. 1) of an inner surface 40 of the carriage 8 by means of several angle irons 41 each having its flanges 42 adjoining to the outer periphery 36 of the casing 31 and inner surface 40 of the carriage 8 and secured to these surfaces 36, 40 by means of washers 43 and bolts 44.

Figure 4:
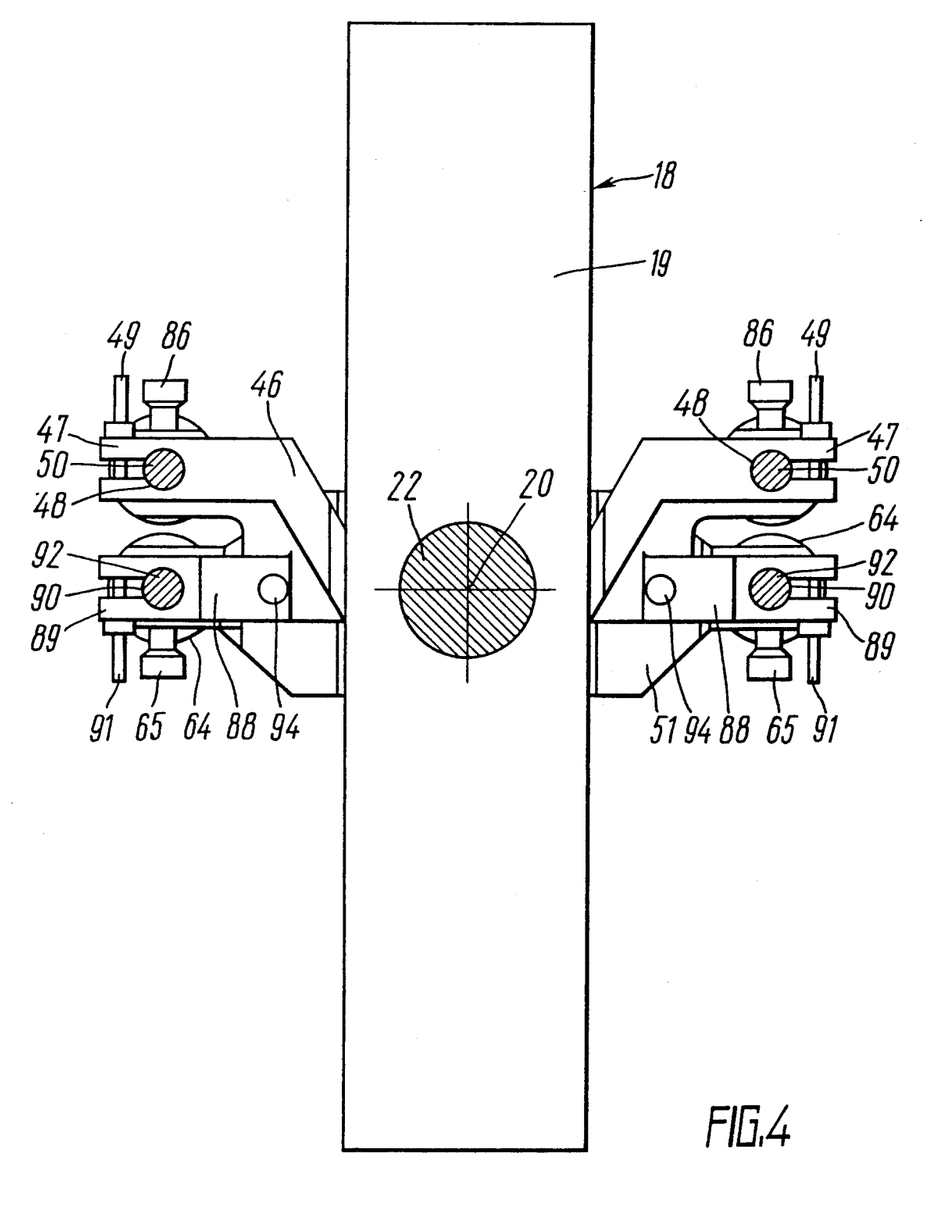
FIG. 4 is a sectional view taken along line IV—IV in FIG. 2 (in a plan view) according to the invention.

An outside member 46 is attached to an inner side 45 (FIG. 2) of the second branch 19 of the dynamometric gauge 18 and is made in the form of a plate secured to the spindle 22 to extend perpendicularly with respect the axis 20 of the rod 12, clamps 47 (FIG. 4) being provided at the ends of the plate. The clamps 47 have holes 48, and stop screws are used to clamp bodies of indentor load pick-ups 50 in these holes to extend in parallel with the axis 20 of the rod 12 on either side of the dynamometric gauge 18.

The apparatus also comprises a means for measuring the depth of penetration of the indentor into the surface of material comprising a frame 51 (FIG. 2) having its opposed bars 52, 53 enclosing the first branch 17 of the dynamometric gauge 18.

Figure 5:
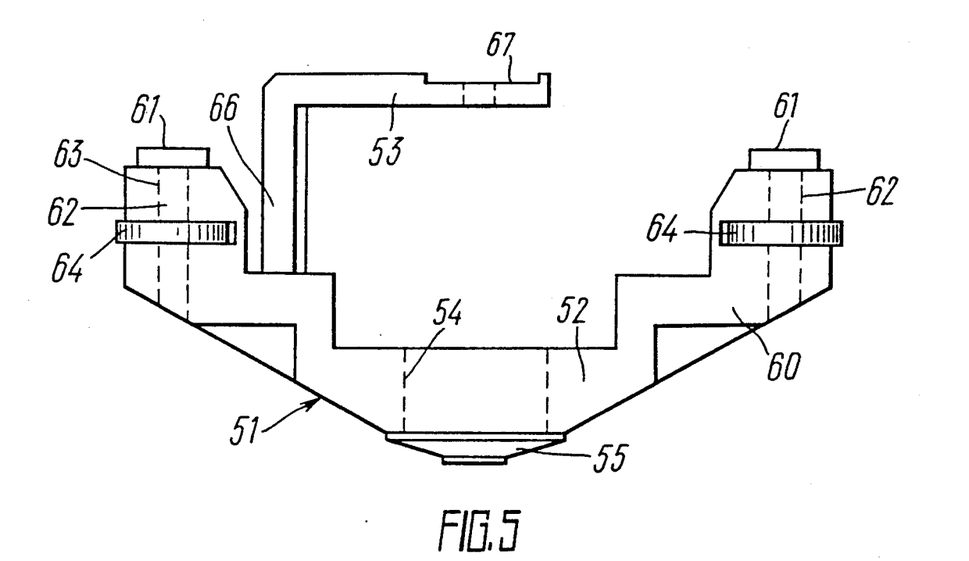
FIG. 5 is a means for measuring the depth of penetration of an indentor (side elevation) according to the invention.
Figure 6:
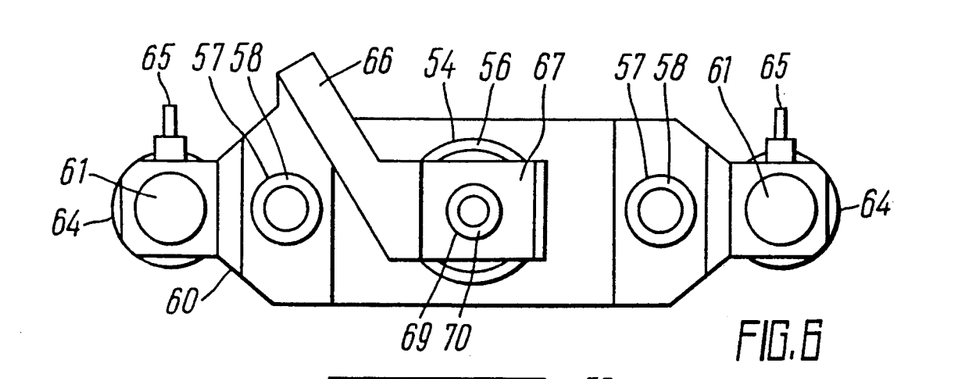
FIG. 6 is ditto of FIG. 5 (plan view) according to the invention.
Figure 7:
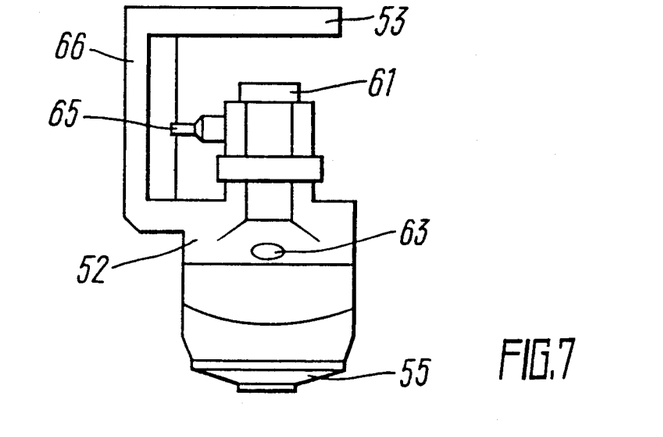
FIG. 7 is ditto of FIG. 5 (front elevation) according to the invention.

The first bar 52 of the frame 51 located between the surface 1 of material and the first branch 17 of the dynametric branch 18 is made in the form of a plate having a tapering bottom side. The first bar 52 of the frame 51 has a hole 54 (FIGS. 2, 5) coaxial with the rod 12. An annular tip 55 is threaded into the hole 54 on the side of the surface 1 of material (FIG. 2), and the indentor 11 is received in the tip in a spaced relation thereto. A bearing 56 having its inner bore receiving the center plate 13 of the rod 12 is received in the hole 54 of the first bar 52 of the frame 51 on the opposite side thereof. A pair of symmetrically positioned holes 57 (FIGS. 2, 6) are made in the periphery of the first bar 52 of the frame 51 to receive bearings 58 (FIG. 2) which are made in the form of bushings each having its bore in which one end of each guide pin 59 is received, the guide pins running in parallel with the axis 20 of the rod 12. Outside members 60 (FIGS. 2,5) are provided as integral parts of, and at the ends of the first bar 52 of the frame 51 and have contact lands 61 on their surfaces. Stems 62 (FIG. 5) are provided at the lower ends of the contact lands 61 which are received in holes 63 of the outside members 60 and on which adjusting nuts 64 are threaded and operatively interact with stop screws 65 (FIGS. 6, 7) in a known way. The holes 63 which receive the stems 63 of the contact lands 61 extend coaxially with the rod 12 (FIG. 2). The first bar 52 of the frame 51 (FIGS. 5, 6, 7) is connected to the second bar 53 by means of an arcuated lateral plate 66 having its curved portion located beyond the lateral side of the first bar 52 of the frame 51.

The second bar 53 (FIGS. 5, 6) of the frame 52 located between the first and second branches 17, 19 (FIG. 2) of the dynamometric branch 18 is in the form of a plate having a groove 67 (FIGS. 2, 5, 6) in its outer side in which an elastic member in the form of an annular spring 68 is received (FIG. 2). A hole 69 is made in the groove 67 of the second bar 53 of the frame 51 to receive a bearing 70 in the form of a bushing. The inner bore of the bearing 70 receives the shank 14 of the rod 12. The annular spring 68 is positioned symmetrically with respect to the axis 20 of the rod 12 has its sides secured to the spindle 22 on the side of the inner surface 45 of the second branch 19 of the dynamometric gauge 18 and to the second bar 53 of the frame 51, respectively. One side 71 of the annular spring 68 is received in a groove 73 made in a surface 74 of the outside member 46 facing towards the surface 1 of material by means of a nut 75 and a retainer ring 76 put on the spindle 22. The other side 72 of the annular spring 68 is secured by means of bolts 77 screwed in the bar 53.

Figure 8:
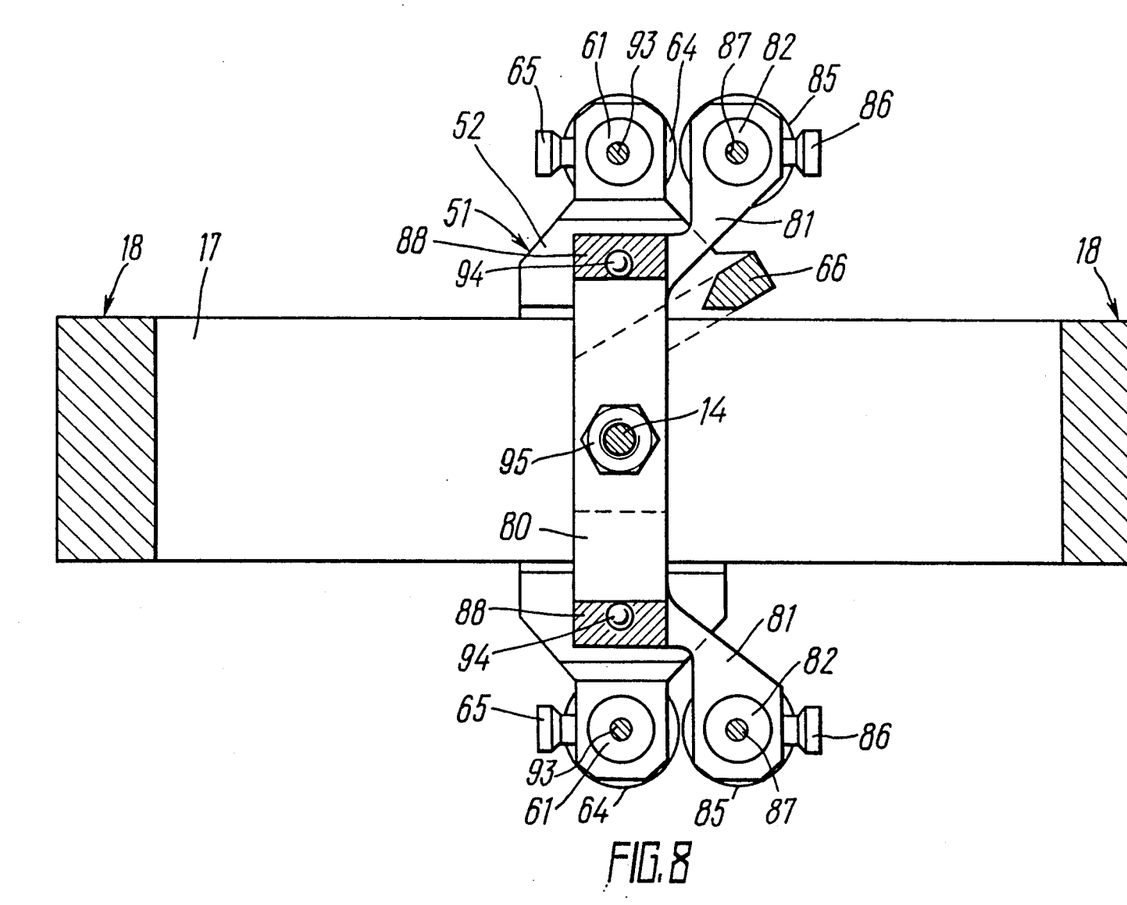
FIG. 8 is a sectional view taken along line VIII—VIII in FIG. 2 (a plan view) according to the invention.

Mounted on an inner side 78 of the first branch 17 of the dynamometric gauge 18 is an outside member 79 which has a base 80 with projections 81 (FIGS. 2, 8) which comprises a plate and which is attached to the innder side 78 (FIG. 2) of the first branch 17 of the dynamometric gauge 18 to extend perpendicularly with respect to the axis 20 of the rod 12. Contact lands 82 are provided on the projections 81 of the base 80 (FIG. 8). A pin 83 is provided on the bottom end of each contact land 82 (FIG. 1) and is received in a hole 84, an adjusting nut 85 being put on the pin. The pin 83 interacts with a stop screw 86. Sensor members 87 of the pick-ups 50 for measuring the indentor load bear against the contact lands 82. The outside member 79 (FIG. 2) also has legs 88 provided on the opposed ends of the base 80 to extend at an angle with respect to the axis 20 of the rod 12. Clamps 89 (FIGS. 2, 4) are provided at the ends of the legs 88 to extend in parallel with the axis 20 of the rod 12. Main holes 90 of the clamps 89 receive bodies of pick-ups 92 (FIG. 2) for measuring the depth of penetration of the indentor into the surface of material clamped by means of stop screws 91 (FIG. 4), the sensor members 93 of the pick-ups being engageable with the contact lands 61 of the outide members 60 provided on the first bar 52 of the frame 51 positioned between the surface 1 of material and the first branch 17 of the dynamometric gauge 18. Auxiliary holes 94 are made in the bottom part of each leg 88, and each guide pin 59 has its second end rigidly secured in the auxiliary hole. The base 80 of the outside member 79 is attached to the innder side 78 of the first branch 17 of the dynamometric gauge 18 by means of a nut 95 threaded on the shank 14 of the rod 21 which is received in a central hole 96 of the base 80 of the outside member 79.

Figure 9:
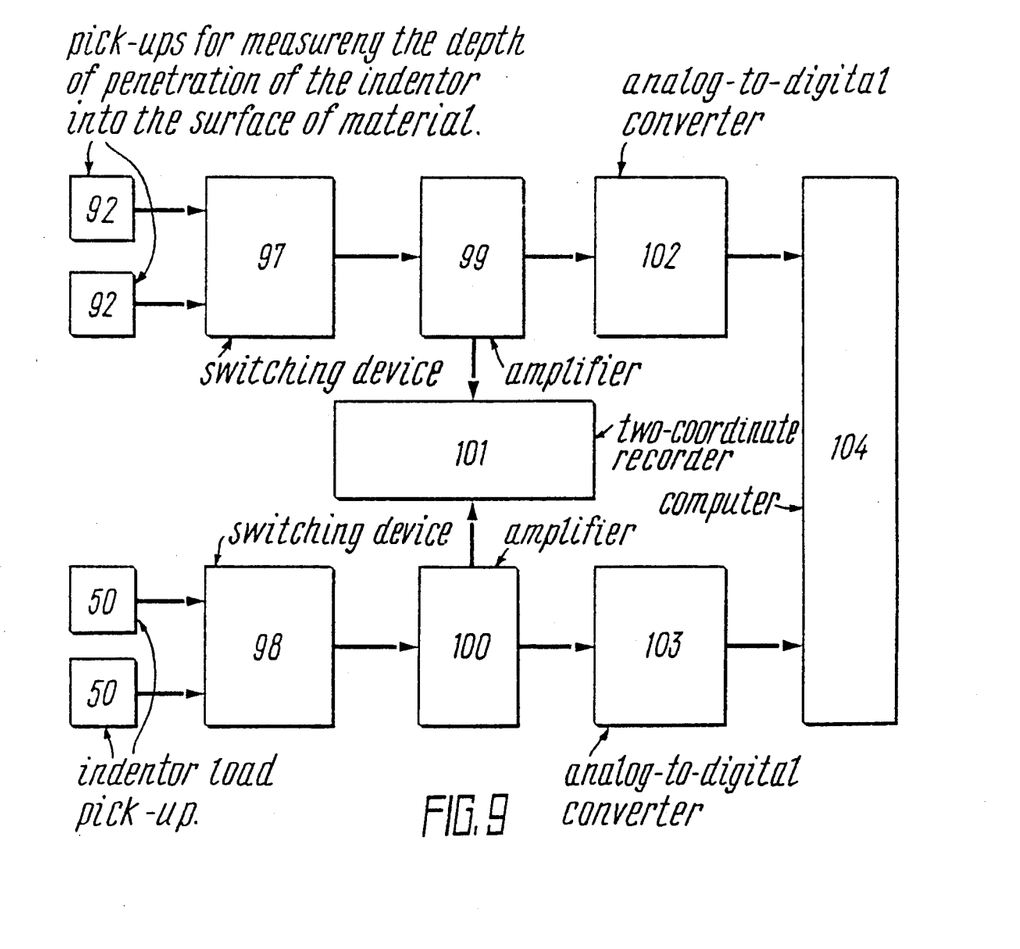
FIG. 9 is an electrical block-diagram of an apparatus for measuring hardness of materials according to the invention.

The pick-ups 50 for measuring the indentor load and the pick-ups 92 for measuring the depth of penetration of the indentor into the surface of material are connected in an electric circuit shown in Fig. 9. Outputs of the pick-ups 50 for measuring the indentor load and of the pick-ups 92 for measuring the depth of penetration of the indentor into the surface of material are connected to inputs of two switching devices 97, 98. Outputs of the switching devices 97, 98 are connected to inputs of signal amplifiers 99, 100, respectively. First outputs of the signal amplifiers 99, 100 are connected to first and second inputs of a two-coordinate recorder 101. Second outputs of the amplifiers 99, 100 are connected to inputs of analog-to-digital converters 102, 103, respectively. Outputs of the analog-to-digital converters 102, 103 are connected to inputs of a computer 104.

The apparatus for measruing hardness of materials functions in the following manner.

The apparatus is used, e.g. for monitoring condition of metal in the casing of a nuclear reactor. (not shown in the drawings). The apparatus is moved by means of handling equipment (not shown in the drawings) into the interior space of the casing of a nuclear reactor, to a chosen spot where hardness of materials is to be measured, e.g. to the zone of weld of the nuclear reactor casing.

The apparatus is attached to the chosen portion of the surface 1 of material (FIG. 1) by switching on a power supply (not shown) of the electromagnets 3 which will have their shoes attracted to the surface 1 of material of the nuclear reactor casing with a force of up to 10 kN.

Measurement of hardness of materials is carried out with remote control from an operator's control board by using connecting cables and a TV-camera owing to the electric drive of the spindle and to the use of electrical pick-ups 50 for measuring the indentor load (FIG. 2) and pick-ups 92 for measuring the depth of penetration of the indentor into the surface of material.

The apparatus is placed in an immediate vicinity to the spot where hardness of material is to be studied on the surface 1 (FIG. 1) of the reactor casing metal by means of the carriage 8 which is moved along the guide planes 9 of the bed 2 by means of an electric motor of the carriage 8 (not shown in the drawings).

When the movable carriage 8 is fixed in an immediate vicinity to the spot of measurement of hardness of material, the electric motor 23 (FIG. 3) of the means for loading the indentor is energized. The shaft 26 of the electric motor 23 rotates the worm 25 which meshes with the gear 27 rotating together with the bushing 28 in the bearings 29. the shaft of the electric motor 23 rotates at a speed which is chosen in accordance with hardness of the material. Rotation of the bushing 28 through the ball-and-screw gearing in the form of a set of the balls 35 ensures the axial movement of the spindle 22 along the axis 20 of the rod so that the dynamometric gauge 18 moves towards the surface 1 of material until the tip 55 of the frame 51 of the means for measuring the depth of penetration of the indentor into the surface of material comes in touch with the surface 1 of material. The use of the ball-and-screw gearing in the form of a set of the balls 35 allows a play in the free fit between the outer periphery of the spindle 22 and the inner surface of the bushing 28 of the means for loading the indentor to be eliminated so as to rule out vibrations of the spindle 22 under the action of the electric motor 23 of the spindle rotary drive and to enhance accuracy of measurement of hardness of materials.

During further movement of the spindle 22 the indentor 11 comes in contact with the surface 1 of material (FIG. 2), and the load upon the surface 1 is then uniformly increased. When both the indentor 11 and the top 55 of the frame 51 of the means for measuring the depth of penetration of the indentor into the surface of material are in contact with the surface 1 of material, the pick-ups 50 and 92 (FIG. 4) will record zero values of the load at the indentor 11 (FIG. 12) and depth of penetration of the indentor 11 into the surface 1 of material.

Calibration and tuning of the pick-ups 50, 92 (FIG. 4) to zero values must be carried out before measuring hardness of materials in a laboratory. The pick-ups 50 (FIGS. 1, 8) are tuned by means of the adjusting nuts 85 threaded on the pins 83 of the contact lands 82 so as to bring the contact lands 82 in engagement with the sensor members 87 of the pick-ups 50. The pick-ups 92 (FIGS. 2, 8) are tuned by means of the adjusting nuts 64 threaded on the stems 62 of the contact lands 61 so as to bring the contact lands 61 in engagement with the sensor members 93 of the pick-ups 92.

For an accurate recording of zero value of the load at the indentor 11 (FIG. 2) and of the depth of penetration of the indentor 11 into the surface 1 of material, the tip 55 of the frame 51 is made in such a manner that the end face of the tip 55 protrudes beyond the vertex of the indentor 11 at a distance of 30 to 50 $\mu$m which depends on the profile of the surface 1 of material and geometry of the indentor 11. qp Accurate initial position of the tip 55 of the frame 51 upon its engagement with the surface 1 of material with respect to the vertex of the indentor 11 and its position in parallel with the surface 1 of material without plays of the frame 51 are achieved owing to the provision of the elastic member in the form of the annular spring 68 which compensates for weight of the frame 51. The force of the annular spring 68 is chosen in such a manner as to rule out penetration of the tip 55 of the frame 51 into the surface 1 of material.

Output signals from the pick-ups 50 (FIG. 4) for measuring the load at the indentor and from the pick-ups 92 for measuring the depth of penetration of the indentor into the surface of material go to inputs of the switching devices 97, 98 (FIG. 9) which add the electric signals. The output signals from the switching devices 97, 98 are fed, via the amplifiers 99, 100, to the inputs of the two-coordinate recorder 101 and analog-to-digital converters 102, 103. The analog-to-digital converters 102, 103 translate the output signals of the pick-ups 50, 92 (FIG. 4) into code of the computer 104 (FIG. 9). The output signals of the analog-to-digital converters 102, 103 are fed to the inputs of the computer 104 where they are stored in a memory (not shown). A chart showing the impression of the indentor 11 (FIG. 2) into the surface 1 of material is recorded in the two-coordinate recorder 101 in the following coordinates: load at the indentor 11 versus depth of penetration of the indentor 11 into the surface 1 of material.

The zero values of the load at the indentor 11 (FIG. 2) and depth of penetration of the indentor 11 into the surface 1 of material are first recorded in the two-coordinate recorder 101 which corresponds to the initial engagement of the end faces of the indentor 11 and tip 55 with the surface 1 of material.

During a further increase in the load at the indentor 11, the indentor 11 penetrates into the surface 1 of material, the dynamometric gauge 18 is deformed, and the sensor members 87 (FIG. 1) of the pick-ups 50 of the indentor load provided on the second branch 19 of the dynamometric gauge 18 cooperate with the contact lands 82 (FIG. 8) provided on the projections 81 of the outside member 79 secured to the first branch 17 (FIG. 12) of the dynamometric gauge 18. As a result of this, values of current load at the indentor 11 are continually recorded in the two-coordinate recorder 101 (FIG. 9) and in the memory of the computer 104.

During penetration of the indentor 11 (FIG. 2) into the surface 1 of material the dynamometric gauge 18 is deformed, and the first branch 17 of the dynamometric gauge 18 cases the legs 88 of the outside member 79 supporting the pick-ups 92 for measuring the depth of penetration of the indentor into the surface of material to move along the guide pins 59. The sensor members 93 of the pick-ups 92 will thus cooperate with the contact lands 61 (FIGS. 2, 8) provided on the outside members 60 of the first bar 52 of the frame 51. As a result, the values of the depth of penetration of the indentor 11 into the surface 1 of material are continually recorded in the two-coordinate recorder 101 (FIG. 9) and in the memory of the computer 104.

During penetration of the indentor 11 (FIG. 2) into the surface 1 of material and deformation of the dynamometric gauge 18 the center plate 13 of the rod 12 moves in the bearings 56 of the first bar 52 of the frame 51, and the guide pins 59 move in the bearings 58 of the outside members 60 so as to rule out plays between the inner surface of the hole 54 of the first bar 52 of the frame 51 and the outer periphery of the center plate 13 of the rod 12 and to reduce a rotary play of the frame 51. This ensures uniform movement of the sensor members 87, 97 of the pick-ups 50, 92 (FIG. 4) without misalignments along the axis 20 of the rod 12 (FIG. 2) so as to enhance immunity of the apparatus to noise and improve accuracy of measurement of hardness of materials.

Placing the pick-ups 50, 92 (FIG. 4) pairwise on eithe rside of the dynamometric gauge 18 ensures compensation for plays in the free fit of the center plate 13 (FIG. 2) and shank 14 of the rod 12 in the frame 51 and enhances accuracy of measurements of hardness of materials.

During penetration of the indentor 11 into the surface 1 of material the tip 55 of the frame 51 sets up the initial level of the surface 1 of material so as to record by means of the pick-ups 92 values of the depth of penetration of the indentor 11 into the surface 1 of material with reference to the initial level of this surface 1 and to enhance accuracy of measurement of hardness of materials. The load at the indentor 11 is raised to a maximum value of the load which is chosen in accordance with hardness of the material being tested, and the electric motor 23 is then switched off, with subsequent exposure at the maximum load, whereafter the electric motor 23 (FIG. 3) is reversed, and the load is relieved from the indentor 11. The elastic member in the form of the annular spring 68 (FIG. 2) compensates for weight of the frame 51 so as to rule out the action of the frame 51 upon the material being tested and to enhance reliability and accuracy of the apparatus.

When the indentor 11 is free from load, the apparatus is retracted from the surface 1 of material by means of the carriage 8 and is moved towards another area of the surface 1 for a next measurement of hardness of materials. After completion of measurements of hardness of materials the apparatus is withdrawn from the casing of the nuclear reactor and radiation monitoring and deactivation are carried out to achieve permissible radiation level. The apparatus makes it possible to monitor the entire kinetics of local deformation of a material under the action of the indentor through three phases of the deformation process: active loading, exposure to a load and load relief from the indentor 11 and to record current values of plastic and elastic deformation. The apparatus also allows local deformation of materials to be carried out within a large range of loads and rates of deformation; microdeformation processes can be studied, macro-and microcreep of materials during the exposure to a load can be recorded, elastic properties of materials and their energy relaxation capacity during deformation can be evaluated by the value of elastic recovery during load relief, and deformability of materials can be assessed.

After handling the data in the computer 104 (FIG. 9) values of standard Brinell hardness, Meyer hardness, ultimate tensile strength, yield limit, uniform deformation and other mechanical properties of materials can be obtained so as to enlarge functional capabilities of the apparatus.

The invention allows construction of the apparatus to be simplified and radioactive exposure of personnel in operation under harmful conditions to be lowered, and technical objects can be tested under harmful conditions, e.g. at nuclear power plants in combination with rapid removal and interchangeability of the apparatus. The invention makes it possible to enlarge functional capabilities of the apparatus so that it can be used for determining coating thickness and to test materials with a low reflectivity (polymers) and brittle materials.

We claim:

1. An apparatus for measuring hardness of materials, said apparatus comprising:
   a rod having an axis; a center plate of said rod having a first end and a second end; a shank of said rod having a first end and a second end; said first end of said shank being secured to said first end of said center plate of said rod;
   an indentor to be pressed into a surface of material secured to the second end of said center plate of the rod;
   a dynamometric gauge having a first branch and a second branch, a longitudinal plane of symmetry which is positioned to extend perpendicularly with respect to said surface of material; the first branch of said dynamometric gauge having an outer surface and an inner surface and a hole in which said shank of said rod is received; the second branch of said dynamometric gauge having an outer surface and an inner surface;
   a means for loading the indentor accommodated in a casing; a spindle of said means for loading the indentor having a periphery and mounted coaxially with said rod on said second branch of said dynamometric gauge; a drive for moving the spindle of said means for loading the indentor which is mechanically coupled to said spindle of said means for loading the indentor;
   at least one pick-up for measuring the load at the indentor having a body and a sensor member, the body being mechanically coupled to one of the branches of said dynamometric gauge; said sensor member of said at least one pick-up for measuring the load at the indentor being engageable with said other branch of said dynamometric gauge;
   a means for measuring the depth of penetration of the indentor into the surface of material in the form of a frame having a first bar and a second bar opposed to each other, a longitudinal plane of symmetry, said first and second bars enclosing said first branch of said dynamometric gauge; said first bar of said frame of said means for measuring the depth of penetration of the indentor into the surface of material having a central part and a peripheral part, being positioned between said surface of material and said first branch of said dynamometric gauge and mounted for movement along said axis of said rod on said center plate of said rod; said second bar of said frame of said means for measuring the depth of penetration of the indentor into the surface of material having a central portion and a peripheral portion, being positioned between said first and second branches of said dynamometric gauge and mounted for movement along said axis of said rod on said shank of said rod; a tip having a first end and a second end and an interior space, the first end of the tip being secured to said first bar of said frame and the second end of tip being engageable with said surface of material; said interior space of said tip receiving the indentor in spaced relation thereto;
   at least one pick-up for measuring the depth of penetration of the indentor into the surface of material having a body and a sensor member, the body being mechanically coupled to said first branch of said dynamometric gauge, the sensor member being engageable with said frame of said means for measuring the depth of penetration of the indentor into the surface of material.

2. An apparatus according to claim 1, wherein said frame of said means for measuring the depth of penetration of the indentor into the surface of material is positioned with respect to said dynamometric gauge in such a manner that said longitudinal planes of symmetry thereof extend perpendicularly with respect to each other.

3. An apparatus according to claim 2, comprising said frame of said means for measuring the depth of penetration of the indentor into the surface of material; said first bar of said frame having a hole in said central portion thereof; said second bar of said frame having a hole in said central portion thereof; a first bearing received in said hole of said first bar of said frame, said center plate of said rod being journalled in said first bearing; a second bearing received in said hole of said second bar of said frame, said shank of said rod being journalled in said second bearing.

4. An apparatus according to claim 2, comprising:
   said at least two pick-ups for measuring the load at the indentor positioned on either side of the longitudinal plane of said dynamometric gauge;
   said at least two pick-ups for measuring the depth of penetration of the indentor into the surface of material positioned on either side of said dynamometric gauge.

5. An apparatus according to claim 2, comprising:
   a first outside member mounted on one of said branches of said dynamometric gauge; at least one main hole in said first outside member, said body of said at least one pick-up for measuring load at the indentor being rigidly secured in said hole;
   a second outside member mounted on said other branch of said dynamometric gauge; at least one contact land provided in said second outside member, said sensor of said at least one pick-up for measuring the load at the indentor being engageable with said contact land;
   a third outside member mounted on said first branch of said dynamometric gauge; at least one main hole in said third outside member, said body of said at least one pick-up for measuring the depth of penetration of the indentor into the surface of material being rigidly secured in said hole;
   a fourth outside member mounted on said first bar of said means for measuring the depth of penetration of the indentor into the surface of material; at least one contact land provided in said fourth outside member, said sensor of said at least one pick-up for measuring the depth of penetration of the indentor into the surface of material being engageable with said contact land.

6. An apparatus according to claim 5, comprising:
   at least one of said outside members having an auxiliary hole;
   one of said bars of said frame of said means for measuring the depth of penetration of the indentor into the surface of material having at least one hole in the peripheral portion thereof; at least one bearing being received in at least one of said holes of one of said bars of said frame;
   at least one guide pin having a first end and a second end, the first end being received in the auxiliary hole of one of said outside members, the second end being received in said at least one bearing of one of said bars of said frame.

7. An apparatus according to claim 6, wherein said at least two guide pins are positioned on either side of the longitudinal plane of symmetry of said dynamometric gauge.

8. An apparatus according to claim 1, comprising said frame of said means for measuring the depth of penetration of the indentor into the surface of material; said first bar of said frame having a hole in said central portion thereof; said second bar of said frame having a hole in said central portion thereof; a first bearing received in said hole of said first bar of said frame; said center plate of said rod being journalled in said first bearing; a second bearing received in said hole of said second bar of said frame, said shank of said rod being journalled in said second bearing.

9. An apparatus according to claim 8, comprising: said at least two pick-ups for measuring the load at the indentor positioned on either side of the longitudinal plane of symmetry of said dynamometric gauge;
said at least two pick-ups for measuring the depth of penetration of the indentor into the surface of material positioned on either side of said dynamometric gauge.

10. An apparatus according to claim 8, comprising;
a first outside member mounted on one of said branches of said dynamometric gauge; at least one main hole in said first outside member, said body of said at least one pick-up for measuring the load at the indentor being rigidly secured in said hole;
a second outside member mounted on said other branch of said dynamometric gauge; at least one contact land provided in said second outside member, said sensor of said at least one pick-up for measuring the load at the indentor being engageable with said contact land;
a third outside member mounted on said first branch of said dynamometric gauge; at least one main hole in said third outside member, said body of said at least one pick-up for measuring the depth of penetration of the indentor into the surface of material being rigidly secured in said hole;
a fourth outside member mounted on said first bar of said means for measuring the depth of penetration of the indentor into the surface of material at least one contact land provided in said fourth outside member, said sensor of said at least one pick-up for measuring the depth of penetration of the indenter into the surface of material being engageable with said contact land.

11. An apparatus according to claim 10, comprising:
at least one of said outside members having an auxiliary hole;
one of said bars of said frame of said means for measuring the depth of penetration of the indentor into the surface of material having at least one hole in the peripheral portion thereof; at least one bearing being received in at least one of said holes of one of said bars of said frame;
at least one guide pin having a first end and a second end, the first end being received in the auxiliary hole of one of said outside members, the second end being received in said at least one bearing of one of said bars of said frame.

12. An apparatus according to claim 11, wherein said at least two guide means are positioned on either side of the longitudinal plane of symmetry of said dynamometric gauge.

13. An apparatus according to claim 8, said apparatus also comprising an elastic member having a first side and a second side opposed to each other, the first side being attached to said spindle of said means for loading the indentor on the side if said inner surface of said second branch of said dynamometric gauge, the second side being attached to said second bar of said frame of said means for measuring the depth of penetration of the indentor into the surface of material.

14. An apparatus according to claim 13, wherein said elastic member is in the form of an annular spring.

15. An apparatus according to claim 1, comprising: said at least two pick-ups for measuring the load at the indentor positioned on either side of the longitudinal plane of symmetry of said dynamometric gauge;
said at least two pick-ups for measuring the depth of penetration of the indentor into the surface of material positioned on either side of said dynamometric gauge.

16. An apparatus according to claim 15, comprising:
a first outside member mounted on one of said branches of said dynamometric gauge; at least one main hole in said first outside member, said body of said at least on pick-up for measuring the load at the indentor being rigidly secured in said hole;
a second outside member mounted on said other branch of said dynamometric gauge; at least one contact land provided in said second outside member, said sensor of said at least one pick-up for measuring the load at the indentor being engageable with said contact land;
a third outside member mounted on said first branch of said dynamometric gauge; at least one main hole in said third outside member, said body of said at least one pick-up for measuring the depth of penetration of the indentor into the surface of material being rigidly secured in said hole;
a fourth outside member mounted on said first bar of said means for measuring the depth of penetration of the indentor into the surface of material; at least one contact land provided in said fourth outside member, said sensor of said at least one pick-up for measuring the depth of penetration of the indentor into the surface of material being engageable with said contact land.

17. An apparatus according to claim 16, comprising:
at least one of said outside members having an auxiliary hole;
one of said bars of said frame of said means for measuring the depth of penetration of the indentor into the surface of material having at least one hole in the peripheral portion thereof; at least one bearing being received in at least one of said holes of one of said bars of said frame;
at least one guide pin having a first end and a second end, the first end being received in the auxiliary hole of one of said outside members, the second end being received in said at least one bearing of one of said bars of said frame.

18. An apparatus according to claim 17, wherein said at least two guide pins are positioned on either side of the longitudinal plane of symmetry of said dynamometric gauge.

19. An apparatus according to claim 15, said apparatus also comprising an elastic member having a first side and a second side opposed to each other, the first side being attached to said spindle of said means for loading the indentor on the side of said inner surface of said second branch of said dynamometric gauge, the second branch being attached to said second bar of said frame of said means for measuring the depth of penetration of the indentor into the surface of material.

20. An apparatus according to claim 19, wherein said elastic member is in the form of an annular spring.

21. An apparatus according to claim 15, wherein said pick-ups for measuring the load at the indentor, said pick-ups for measuring the depth of penetration of the indentor into the surface of material and said drive for moving the spindle of said means for loading the indentor are electrical.

22. An apparatus according to claim 21, comprising said means for loading the indentor; a worm gearing of said means for loading the indentor coupled to said electric drive for moving the spindle; a ball-and-screw gearing of said means for loading the indentor operatively connected to said worm gearing and provided on said periphery of said spindle.

23. An apparatus according to claim 1, comprising:
- a first outside member mounted on one of said branches of said dynamometric gauge; at least one main hole in said first outside member, said body of said at least one pick-up for measuring the load at the indentor being rigidly secured in said hole;
- a second outside member mounted on said other branch of said dynamometric gauge; at least one contact land provided in said second outside member, said sensor of said at least one pick-up for measuring the load at the indentor being engageable with said contact land;
- a third outside member mounted on said first branch of said dynamometric gauge; at least one main hole in said third outside member, said body of said at least one pick-up for measuring the depth of penetration of the indentor into the surface of material being rigidly secured in said hole;
- a fourth outside member mounted on said first bar of said means for measuring the depth of penetration of the indentor into the surface of material; at least one contact land provided in said fourth outside member, said sensor of said at least one pick-up for measuring the depth of penetration of the indentor into the surface of material being engageable with said contact land.

24. An apparatus according to claim 23, comprising:
- at least one of said outside members having an auxiliary hole;
- one of said bars of said frame of said means for measuring the depth of penetration of the indentor into the surface of material having at least one hole in the peripheral portion thereof; at least one bearing being received in at least one of said holes of one of said bars of said frame;
- at least one guide pin having a first end and second end, the first end being received in the auxiliary hole of one of said outside members, the second end being received in said at least one bearing of one of said bars of said frame.

25. An apparatus according to claim 24, wherein said at least two guide pins are positioned on either side of the longitudinal plane of symmetry of said dynamometric gauge.

26. An apparatus according to claim 24, said apparatus also comprising an elastic member having a first side and a second side opposed to each other, the first side being attached to said spindle of said means for loading the indentor on the side of said inner surface of said second branch of said dynamometric gauge, the second side being attached to said second bar of said frame of said means for measuring the depth of penetration of the indentor into the surface of material.

27. An apparatus according to claim 26, wherein said elastic member is in the form of an annular spring.

28. An apparatus according to claim 24, wherein said pick-ups for measuring the load at the indentor, said pick-ups for measuring the depth of penetration of the indentor into the surface of material and said drive of the spindle of said means for loading the indentor are electrical.

29. An apparatus according to claim 28, comprising said means for loading the indentor; a worm gearing of said means for loading the indentor coupled to said electric drive for moving the spindle; a ball-and-screw gearing of said means for loading the indentor operatively connected to said worm gearing and provided on said periphery of said spindle.

30. An apparatus according to claim 23, said apparatus also comprising an elastic member having a first side and a second side opposed to each other, the first side being attached to said spindle of said means for loading the indentor on the side of said inner surface of said second branch of said dynamometric gauge, the second branch being attached to said second bar of said frame of said means for measuring the depth of penetration of the indentor into the surface of material.

31. An apparatus according to claim 30, wherein said elastic member is in the form of an annular spring.

32. An apparatus according to claim 23, wherein said pick-ups for measuring the load at the indentor, said pick-ups for measuring the depth of penetration of the indentor into the surface of material and said drive for moving the spindle of said means for loading the indentor are elecrical.

33. An apparatus to claim 32, comprising said means for loading the indentor; a worm gearing of said means for loading the indentor coupled to said electric drive for moving the spindle; a ball-and-screw gearing of said means for loading the indentor operatively connected to said worm gearing and provided on the periphery of said spindle.

34. An apparatus according to claim 1, said apparatus also comprising an elastic member having a first side and a second side opposed to each other, the first side being attached to said spindle of said means for loading the indentor on the side of said inner surface of said second branch of said dynamometric gauge, the second side being attached to said second bar of said frame of said means for measuring the depth of penetration of the indentor into the surface of material.

35. An apparatus according to claim 34, wherein said elastic member is in the form of an annular spring.

36. An apparatus according to claim 34, wherein said pick-ups for measuring the load at the indentor, said pick-ups for measuring the depth of penetraton of the indentor into the surface of material and said drive of the spindle of said means for loading the indentor are electrical.

37. An apparatus according to claim 36, comprising said means for loading the indentor; a worm gearing of said means for loading the indentor coupled to said electric drive for moving the spindle; a ball-and-screw gearing of said means for loading the indentor operatively connected to said worm-gearing and provided on said periphery of said spindle.

38. An apparatus according to claim 1, wherein said pick-ups for measuring the depth of penetration of the indentor into the surface of material and said drive for moving the spindle of said means for loading the indentor are electrical.

39. An apparatus according to claim 38, comprising said means for loading the indentor; a worm gearing of said means for loading the indentor coupled to said electric drive for moving the spindle; a ball-and-screw gearing of said means for loading the indentor operatively connected to said worm gearing and provided on said periphery of said spindle.

* * * * *